United States Patent [19]

Schindler et al.

[11] 4,236,987
[45] Dec. 2, 1980

[54] ELECTRODE HAVING MEMBRANE WITH ION SELECTIVE PROPERTIES

[75] Inventors: Johannes G. Schindler, Marburg an der Lahn; Wilfried Schael, Bad Homburg von der Hohe, both of Fed. Rep. of Germany

[73] Assignee: Dr. E. Fresenius Chemisch Pharmazeutische Industrie KG Apparatebau KG, Bad Homburg von de Hohe, Fed. Rep. of Germany

[21] Appl. No.: 960,167

[22] Filed: Nov. 13, 1978

[30] Foreign Application Priority Data

Nov. 14, 1977 [DE] Fed. Rep. of Germany ....... 2750807

[51] Int. Cl.³ ............................................. G01N 27/30
[52] U.S. Cl. ................................ 204/195 M; 204/296; 260/29.1 SB
[58] Field of Search ............ 260/29.1 SB; 204/195 M, 204/195 L, 1 A, 296

[56] References Cited

U.S. PATENT DOCUMENTS

| | | | |
|---|---|---|---|
| 3,428,707 | 2/1969 | Amos et al. | 260/29.1 SB X |
| 3,709,811 | 1/1973 | Saunders | 204/195 M |
| 3,751,519 | 8/1973 | Bostick et al. | 260/29.1 SB X |
| 3,767,553 | 10/1973 | Brown et al. | 204/195 M |
| 3,796,681 | 3/1974 | Ratliff et al. | 260/29.1 SB X |
| 3,994,995 | 11/1976 | Frey et al. | 260/29.1 SB X |
| 4,129,543 | 12/1978 | Kaplan | 260/29.1 SB |
| 4,130,530 | 12/1978 | Mark et al. | 260/29.1 SB |
| 4,133,735 | 1/1979 | Afromowitz et al. | 204/195 M X |
| 4,135,999 | 1/1979 | Schindler et al. | 204/195 M |

FOREIGN PATENT DOCUMENTS 88543 3/1976 Japan ............... 260/29.1 SB

OTHER PUBLICATIONS

G. R. J. Christoffersen et al., Analytical Chimica Acta, 81, pp. 191-195, (1976).
R. P. Kraig et al., Science, vol. 194, No. 4266, pp. 725-726, (1976).

Primary Examiner—G. L. Kaplan
Attorney, Agent, or Firm—Omri M. Behr; Martin Sachs

[57] ABSTRACT

There is provided a novel type of ion selective membrane comprising a non-ion selective carrier, and an ion selective active phase molecule having a hydrophilic segment and a lipophilic periphery. In the preferred embodiment said molecule is a siloxane molecule whose Si-O-Groups are open chain, branch chain or cyclically oriented. These ion selective membranes are useful in the selective detection of alkali- and alkaline-earth metals. There is further provided an electrode for use with such a membrane.

8 Claims, 3 Drawing Figures

ELECTRODE HAVING MEMBRANE WITH ION SELECTIVE PROPERTIES

DESCRIPTION OF THE PRIOR ART

The selectivity properties of ion sensitive electrodes thereof are determined to a substantial extent by the ion selective membrane utilized therewith. The classical example of this is the glass membrane which is utilized for the determination of hydrogen ion concentration (pH electrodes). Similarly, electrodes with glass membranes have become known for the measurement of sodium and potassium cations.

Other forms of ion selective membranes comprise a substantially non-selective carrier material for example polyvinyl chloride, including, if desired, plasticizer components, into which the ion active substance is introduced. In contrast to the glass membranes this technology is far more flexible and provides for the utilization of the membrane for different technical purposes.

Such membranes are usually produced by dissolving an organic polymer in a suitable, usually substantially volatile solvent, introducing the ion active substance into the solution, if necessary with the addition of plasticizers, softening agents, other substantially nonvolatile solvents, and the like which influence the density and consistency of the membrane.

The homogeneous mixture may then be poured onto a glass sheet from which, after evaporation of the solvent, the membrane may be peeled. Another mode of preparation comprises in mixing the polymer, solvent, plasticizer or the like, and ion active phase and soaking a suitable carrier therewith.

As carriers there may also be mentioned glass sinters, fibrous materials, woven and non-woven fabrics, suitably fibrous fabrics made of non-ion selective materials.

It is known that the glass membranes can only be made selective for very few types of ions and furthermore possess certain somewhat undesirable properties. Therefore, further ion selective substances have long been sought. In this connection, certain carrier antibiotics have been considered to possess great promise. Among these may be mentioned valinomycin, nonactin and crown ethers (German Pat. No. 1,648,987) see also K. Cammann "Das Arbeiten mit ionenselektiven Electroden", (translation: "Working With Ion Selective Electrodes") 2nd Edition, Springer-Verlag Berlin-Heidelberg—New York 1977, p. 29 and 81.

Regrettably the above-named substances are natural products which are not only difficult to obtain but are also extremely expensive. This problem of availability and cost also applies to synthetic products of this type. The common property of these materials is that the molecule comprises a hydrophilic moiety suitably a skeletal moiety in the form of or capable of providing a central core, opening or concavity and a lipophilic periphery around said core. Such materials work as complexing agents into whose molecular cavity predetermined cations can be occluded.

It would be desirable to provide membranes of the foregoing type having a higher selectivity for predetermined ions in particular for those members of the alkali- and alkaline-earth group whose detection is required by analytical practice. Such membranes should possess a constant and predictable quality and reasonable shelf life as well as having production costs below those of heretofore known substances.

SUMMARY OF THE INVENTION

It has been found that polar silicone containing polymers, in particular siloxanes, in the form of open chains, branch chains or cyclic form have a comparatively simple structure and, having a substantially inorganic skeleton, possess excellent shelf life.

They may also be provided in dimensions and special configurations to exhibit a preference for certain predetermined cations. In a similar manner to the known complex forming agents (ie carrier antibiotics and crown ethers) the siloxanes possess the property of unsymmetrical loading, in particular, they possess a substantial negative loading in an oriented concave, more or less closed, intra-molecular environment. This concavity may be predetermined to possess dimensions and spacial configuration which is particularly suitable for the occlusion therein of certain positively charged ions of particular dimensions.

It should be noted that the formation of the concavities often occurs at the moment of complexing due to certain electrostatic exchanges between the ligands of the ion selective material and the ion to be occluded. This circumstance explains why it is possible for an open chain molecule as well as a cyclic one to possess these desirable qualities.

The selected metal ion takes part in the complexing procedure in a manner which follows, to a certain extent, the principle of optimal space occupancy in which the oxygen atoms taking part in the complexing procedure serve as a replacement for the hydrating shell of the complexed ion. The several neighboring polar oxygen atoms provide the hydrophilic environment in the interior of the molecule for the complexing of the cations while the remaining portion of the molecules are responsible for the principally lipophilic properties on the periphery of the thus formed complex.

DESCRIPTION OF THE PREFERRED EMBODIMENTS

Figure 1:
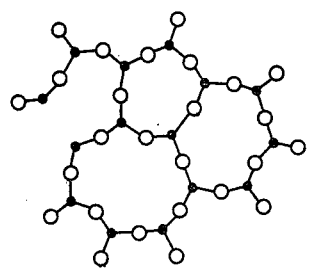
FIG. 1 is a schematic diagram of the molecular skeleton of quartz glass.

FIG. 1 illustrates why glass electrodes are of limited utility with respect to selectivity. The silicon atoms are shown as black circles while the oxygen atoms are shown as white circles. Of the four valences of the silicon atom only three are shown, the fourth points out of the paper and operates as the complexing ligand in molecular framework. It wil be noted that the atoms are formed in irregular rings and open spaces so that in the open spaces, entering foreign ions of a different dimension may find room. As a consequence of this irregularity only a rather limited specificity of selectivity is to be expected from glass.

Figure 2:
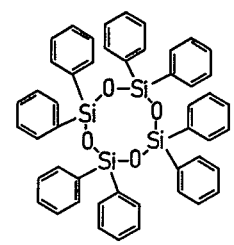
FIG. 2 shows the molecular structure of a preferred ion selective material of the present invention, namely, octaphenylcyclotetrasiloxane.

The predetermined spacial relationship which is established utilizing the membranes of the present invention is illustrated by FIG. 2.

The four silicon atoms and the four oxygen atoms define an opening of predetermined dimensions which similarly permits the acceptance therein of cation of known dimensions, for example lithium ions, in the course of complex formation in which procedure the oxygen in particular participates. The eight phenyl moieties which surround the periphery of the molecule, on the other hand, possess strong lipophilic properties. Other polysiloxanes have other cavities which of course can be fitted to the dimensions of other cations.

Instead of the phenyl ring other substituents may be utilized as the peripheral groups of the siloxane complex. These groups include alkyl, suitably lower alkyl of 1 to 5 carbon atoms such as methyl, ethyl, propyl or butyl, alkenyl, suitably lower alkenyl of 2 to 5 carbon atoms such as vinyl; substituted phenyl suitably alkyl phenyl most suitably lower alkyl phenyl of 1 to 5 carbon atoms such as tolyl; cycloalkyl suitably cycloalkyl of from 4 to 7 carbon atoms such as cyclobutyl, cyclopentyl, cyclohexyl or cycloheptyl; alkoxy, suitably lower alkoxy of 1 to 5 carbon atoms most suitably butoxy and halogenated lower alkoxy of 1 to 5 carbon atoms for example chloroethoxy. Ester groups such as alkylcarboxy suitably ethylcarboxy may be employed, as may be alkylenedioxy suitably lower alkylenedioxy of 2 to 5 carbon atoms such as ethylenedioxy. The substituents on the siloxane complex are not limited to organic substitutents. They may include hydrogen and halogen for example fluorine, chlorine, bromine and iodine. Furthermore, the substituents on the siloxane nucleus need not all be the same. A combination of up to three of any of the foregoing substituent moieties may be employed.

As stated herein above, the selectivity of the membranes for predetermined alkali and alkaline-earth metal ions can be determined by selecting a siloxane having a particular number of co-ordination points (oxygen atoms).

The optimal number of co-ordination points (oxygen atoms) were determined by studies caried out by Morf and Simon (Helv. Chim. Acta. 54 (1971)) in a paper entitled (in translation) "Studies of the Ion Selectivity with respect to alkali and alkaline-earth metal ions by electrically neutral carrier antibiotics and model combinations". Morf et al suggests the following situations:

For alkali ions a maximum of 6 co-ordination points
For $Be^{++}$ 4 co-ordination points
For $Mg^{++}$ 6 co-ordination points
For $Ca^{++}$, $Sr^{++}$, and $Ba^{++}$ 8 co-ordination points with increasing size of the ligand shell the selectivity moves in the direction of choice of the alkali ions.

The carriers utilized in the present invention are materials which possess no detectable or negligible ion selective properties. Such carriers fall in two categories. The first category comprises thermoplastic material into which the ion selective material is intimately incorporated in a manner set forth in detail herein below and the second group comprises carriers upon which or between the interticies of which the active material is absorbed. It will be understood by those skilled in the art that under certain circumstances the actual dividing line between these two groups may be somewhat vague. The division, therefore, is made for purposes of convenience only.

In making a membrane of the first category, the thermoplastic material is taken up in a suitable solvent. Among the thermoplastic materials that may be mentioned, polyvinyl chloride and nitro cellulose are especially preferred. A predetermined amount of the ion selective material, suitably the siloxane, is added thereto. The solvent is then permitted to evaporate to leave a residual membrane. It is especially preferred, however, to place a small amount of this solution into the body of the electrode in which the membrane is to be utilzed (where this is the ultimate use) so that the membrane is cleanly and intimately formed in situ. This procedure may be repeated from 1 to 10 times, preferably from 4 to 7 times, to provide, in the case of electrodes, a total layer thickness of between 0.3 and 0.7 millimeters, most suitably 0.5 millimeters. The ratio of the active phase to the carrier phase may vary. However, a ratio of between 2:1 to 1:10 is suitable, a ratio of approximately 1:1 being especially preferred. The amount of solvent utilized is not critical. The amount utilized should be sufficient to solvate the components and keep them in solution while the membrane forming operations are performed. Thus a solution of 15% by weight of the carrier such as polyvinyl chloride in the solvent, for example cyclohexanone has been found operative.

It has been found that the selectivity of the membranes produced in this manner may be enhanced with respect to particular ions by adding thereto certain compounds known to the thermoplastic art as plasticizers or softeners. These materials are generally substantially involatile (at ambient temperature and pressure) organic solvents capable of dissolving the thermoplastic carrier. Examples of such plasticizers which have been found useful in the context of the present invention include Tris(2-ethylhexyl phosphate), dinonyl phthalate, various sebecate derivatives, diphenylethers, and ortho nitro phenyl octyl ether. Use of the first two materials enhances the detection of lithium, sodium, and ammonium ions, the third and fourth are suitable for enhancing the detection of potassium ions and the fifth may be used for enhancing the detection of calcium ions. These plasticizers may be utilized, relative to the carrier, in a ratio of between about 3:1 to about 1:5, suitably from between 1:1 to about 2:1.

The use of the membranes of the present invention is in no way restricted to their use in electrodes. They may also be employed as desalination agents, for example for the de-ionization of water. One particularly interesting and useful embodiment of the invention is its use in the so-called fluid membranes. These membranes comprise solid, non-thermoplastic carriers having the active, ion selective material, absorbed thereon. Examples of such carriers for fluid membranes are porous materials such as ceramics, suitably in the unglazed state, sintered glass, woven and non-woven fibrous fabrics including felt, and the like. Sintered substantially non-thermoplastic materials such as, for example, sintered polytetrafluorethylene may also be employed as the carrier. In the formation of fluid membranes a solution of the active material is prepared in a suitable solvent, the carrier material is soaked with this solution which is then permitted to drain out and the solvent permitted to evaporate from the retained solution in the usual manner. The active material may also be directly absorbed.

As stated heretofore, the membranes of the present invention may be utilized to form an ion selective electrode.

Figure 3:
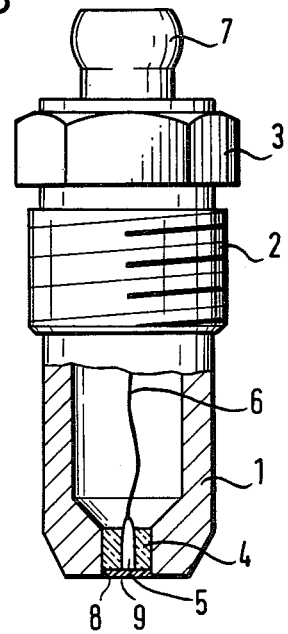
FIG. 3 shows an ion selective electrode as an example of the use of the membrane of the present invention containing the new substances.

FIG. 3 shows an ion selective electrode as an example of the use of the membrane of the present invention containing the new substances. The body of the electrode 1, which is provided with a screw threaded head 2 and a hexagonal nut head, may be introduced into a flow-through chamber. The electrode body 1 is provided with a central axial opening and a further axial cylindrical boring, the latter being partially filled by cylinder 4 of polyacrylate. This cylinder 4 is further provided with a central platinum rod 5 whose head portion coincides with the outer surface of the polyacrylate cylinder. The platinum rod 5 is connected via wire 6 to the central contact of a coaxial connector 7. The membrane 9 is located in the space provided between the bottom surface of the electrode body and the indentation therein, between the level of said head portion of body 1 and the head portion of the platinum rod 5 in opening 8. The membrane comprises substantially a layer of polyvinyl chloride having a siloxane as ion active substance provided therein.

EXAMPLE I

Octaphenylcyclotetrasiloxane (300 mg) is taken up in Tris(2-ethylhexyl-phosphate (1 ml), there is added thereto a solution of polyvinyl chloride in cyclohexanone (15%, 3 ml) the Tris(ethylhexyl)phosphate serves as a plasticizer. A drop of the thus formed polymer solution is placed in space 8 of the electrode of FIG. 3. After evaporation of the solvent the electrode is ready for use. If desired, further layers may be formed in a similar manner.

The electrode formed in the manner set forth above has selective properties with respect to alkali and alkaline earth metal ions. Where the sensitivity for hydrogen ions is arbitrarily set as 1 then the sensitivity for other ions is as follows: $Li^+$ $7\times10^{-2}$, $K^+$ $1.5\times10^{-3}$, $Na^+$ $6\times10^{-3}$, $NH_4^+$ $1.5\times10^{-2}$, $Ca^{++}$ $7\times10^{-6}$, $Mg^{++}$ $1\times10^{-6}$. The electrode can therefore, for example, be utilized in place of the conventional glass membrane electrode in certain cases as a pH sensor.

EXAMPLE II

In accordance with the procedure of Example I but utilizing a solution of polyvinylchloride in cyclohexanone (15%, 4.5 ml) together with Tris(2-ethyl-hexyl)-phosphate (0.5 ml) and Polycyclosiloxan AN 175 (Wacker Chemie) (1.5 ml) there is produced a membrane which shows a sensitivity of 51 mV/decade for protons (measured between $10^{-4}$ M HCl and $10^{-3}$ M HCl) and the following selectivity coefficients: $K_{H-Na}=4.33\times10^{-2}$; $K_{H-K}=6.02\times10^{-2}$; $K_{H-NH4}=7.58\times10^{-2}$; $K_{H-Ca}=1.13\times10^{-2}$; $K_{H-Mg}=1.0\times10^{-2}$;

Similarly, but where in place of polycyclosiloxane there is utilized tetramethyldivinyldisiloxane VSi2 (Wacker Chemie) (1.5 ml) (and utilizing the same two other components in the same ratios) there is obtained a membrane which shows a sensitivity of 56 mV/decade for protons (measured between $10^{-4}$ M HCl and $10^{-3}$ M HCl) and the following selectivity coefficients: $K_{H-Na}=8.39\times10^{-3}$; $K_{H-K}=4.56\times10^{-3}$; $K_{H-NH4}=2.64\times10^{-2}$; $K_{H-Ca}=1.26\times10^{-3}$; $K_{H-Mg}=2.6\times10^{-3}$;

Similarly, but where in place of polycyclosiloxane, and utilizing the same two other components in the same ratios, there is utilized Methylsiloxane 200 fluid 1 cs AFX 189 (Dow Corning) (1.5 ml) there is obtained a membrane which shows a sensitivity of 57 mV/decade for protons (measured between $10^{-4}$ M HCl and $10^{-3}$ M HCl) and the following selectivity coefficients: $K_{H-Na}=1.05\times10^{-2}$; $K_{H-K}=1.07\times10^{-2}$; $K_{H-NH4}=3.33\times10^{-2}$; $K_{H-Ca}=2.32\times10^{-3}$; $H_{H-Mg}=2.21\times10^{-3}$.

EXAMPLE III

Fluid membrane

A disc of sintered porous polytetrafluorethylene is placed in a bath containing a mixture of n-methyl-ethyl cyclosiloxane (n=3–6) and the surrounding pressure reduced, at ambient temperature, to between 1 to 0.1 mmHg. The reduced pressure is maintained until no further bubbling is observed from the disc which is totally immersed in the siloxane. Ambient pressure is then restored, and the disc removed from the siloxane solution and permitted to drain. The thus produced fluid membrane has a high ratio of cation to anion transfer in electrodialysis units. This ratio may be further amplified by the addition to the siloxane mixture of sodium tetraphenyl borate in a borate to siloxane ratio of from 3:1 to 1:3.

We claim:

1. An ion selective electrode, being selective with respect to predetermined alkali or alkaline-earth metal ions comprising:
   (a) a membrane comprising
      (i) a carrier membrane composed of a non-ion selective carrier material and
      (ii) an ion selective material in intimate contact with said carrier, said ion selective material comprising at least one predetermined molecular species exhibiting ion selectivity with respect to predetermined alkali or alkaline-earth metal ions said molecular species being selected from the group consisting of open chain, branch chain or cyclic siloxanes comprising a plurality of Si-O-Groups, the oxygen atoms of said siloxanes having hydrophilic properties and said siloxanes being substituted by lipophilic moieties, further including
   (b) electrical conducting means in intimate contact with said membrane.

2. An electrode in accordance with claim 1 wherein the lipophilic substitutents are selected from the group consisting of lower alkyl of 1 to 5 carbon atoms, lower alkenyl of 2 to 5 carbon atoms, cycloalkyl of 4 to 7 carbon atoms, lower alkoxy or halo lower alkoxy of 1 to 5 carbon atoms, phenyl, lower alkyl phenyl of 1 to 5 carbon atoms in the lower alkyl moiety, lower alkylcarboxy of 1 to 5 carbon atoms in the alkyl moiety, lower alkylene dioxy of 2 to 5 carbon atoms, hydrogen and halogen.

3. An electrode in accordance with claim 2 wherein the siloxane moiety is substituted by one, two or three of the substituent moieties set forth in claim 2.

4. An electrode in accordance with claim 1 wherein the carrier is a polymeric material selected from the group consisting of polyvinyl chloride, and nitro cellulose.

5. An electrode in accordance with claim 1 wherein the carrier material is ceramic, sintered glass, felt, woven and non-woven fiber containing fabrics having the ion selective material absorbed thereon.

6. An electrode according to claim 1 further comprising a plasticizer.

7. An electrode according to claim 6 wherein the plasticizer is a polar organic material capable of dissolving the carrier and being substantially non-volatile at ambient temperature and pressure.

8. An electrode in accordance with claim 6 wherein the plasticizer is selected from the group consisting of Tris(2-ethylhexyl phosphate), dinonyl phthalate sebesate derivatives, diphenylether, and ortho nitro phenyl octyl either.

* * * * *